United States Patent [19]

Watmough et al.

[11] Patent Number: 4,889,122
[45] Date of Patent: Dec. 26, 1989

[54] DIVERGENT ULTRASOUND ARRAYS

[75] Inventors: David Watmough, Banchory, Scotland; Kwok K. Chan, Sheffield, United Kingdom

[73] Assignee: Aberdeen University, Scotland

[21] Appl. No.: 180,346

[22] Filed: Apr. 11, 1988

Related U.S. Application Data

[63] Continuation of Ser. No. 936,246, Dec. 1, 1986, abandoned.

[30] Foreign Application Priority Data

Nov. 29, 1985 [GB] United Kingdom ............... 8529446

[51] Int. Cl.⁴ .............................................. A61F 7/00
[52] U.S. Cl. ............................... 128/399; 128/660.03; 128/24 A

[56] References Cited

U.S. PATENT DOCUMENTS

| | | | |
|---|---|---|---|
| 3,552,382 | 1/1971 | Mount | 128/662 |
| 4,343,301 | 8/1982 | Indech | 128/24 A |
| 4,391,281 | 7/1983 | Green | 128/660 |
| 4,441,486 | 4/1984 | Pounds | 128/24 A |
| 4,586,512 | 5/1986 | Do-huu et al. | 128/660 |
| 4,622,972 | 11/1986 | Giebeler, Jr. | 128/24 A X |
| 4,646,756 | 3/1987 | Watmough et al. | 128/24 A X |
| 4,658,828 | 4/1987 | Dory | 128/660 |
| 4,696,299 | 9/1987 | Shene et al. | 128/24 A X |
| 4,718,421 | 1/1988 | Rohwedder et al. | 128/660 |

OTHER PUBLICATIONS

Lehman, J. F. ed., "Therapeutic Heat and Cold", Waverly Press, Baltimore, Md. ©1982 pp. 366–369, 502–505 (copy AU335).

Primary Examiner—Francis Jaworski
Attorney, Agent, or Firm—Ostrolenk, Faber, Gerb & Sofffen

[57] ABSTRACT

An ultrasound hyperthermia unit for the treatment of a target tissue, includes an ultrasound transducer array (1) angled to direct sonic energy toward a target (8), wherein the array (1) comprises a plurality of divergent transducers (2) arranged radially of a central axis to provide a coherent treatment field about a central axis.

Temperature sensing means (10) may be operatively associated with the array and adapted to provide an output signal indicative of temperature values adjacent a target tumour, said signal being utilized to control the output of the transducers.

A liquid bath (5) may be provided for being located between the array (1) and the skin (14) of a patient, said liquid bath being adapted to warm or induce local hyperthermia in the skin surface. The divergent array, when associated with a water bath, allows a particularly effective treatment of physiotherapeutic conditions or neoplastic tissues without causing collateral damage.

25 Claims, 16 Drawing Sheets

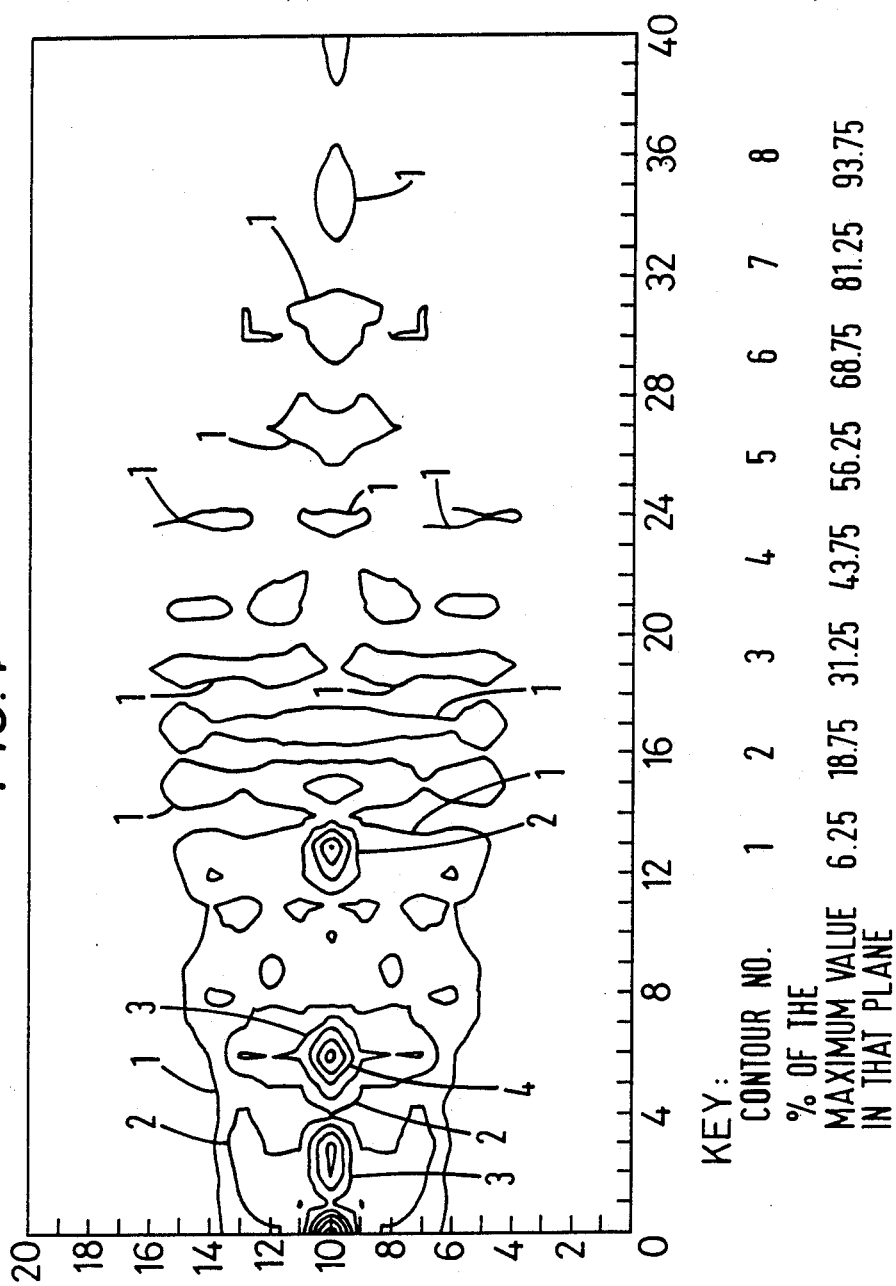

KEY:

| CONTOUR NO. | % OF THE MAXIMUM VALUE IN THAT PLANE |
|---|---|
| 1 | 6.25 |
| 2 | 18.75 |
| 3 | 31.25 |
| 4 | 43.75 |
| 5 | 56.25 |
| 6 | 68.75 |
| 7 | 81.25 |
| 8 | 93.75 |

KEY:

| CONTOUR NO. | % OF THE MAXIMUM VALUE IN THAT PLANE |
|---|---|
| 1 | 6.25 |
| 2 | 18.75 |
| 3 | 31.25 |
| 4 | 43.75 |
| 5 | 56.25 |
| 6 | 68.75 |
| 7 | 81.25 |
| 8 | 93.75 |

| KEY: CONTOUR NO. | TEMP. (°C) |
|---|---|
| 1 | 38.4 |
| 2 | 39.5 |
| 3 | 40.6 |
| 4 | 41.7 |
| 5 | 42.8 |
| 6 | 43.9 |
| 7 | 45.0 |
| 8 | 46.1 |
| 9 | 47.2 |

| KEY: | CONTOUR NO. | TEMP. (°C) |
|---|---|---|
| | 1 | 38.4 |
| | 2 | 39.5 |
| | 3 | 40.6 |
| | 4 | 41.7 |
| | 5 | 42.8 |
| | 6 | 43.9 |
| | 7 | 45.0 |
| | 8 | 46.1 |
| | 9 | 47.2 |

| KEY: | CONTOUR NO. | TEMP. (°C) |
|---|---|---|
| | 1 | 38.4 |
| | 2 | 39.5 |
| | 3 | 40.6 |
| | 4 | 41.7 |
| | 5 | 42.8 |
| | 6 | 43.9 |
| | 7 | 45.0 |
| | 8 | 46.1 |
| | 9 | 47.2 |

| KEY: CONTOUR NO. | TEMP. (°C) |
|---|---|
| 1 | 38.4 |
| 2 | 39.5 |
| 3 | 40.6 |
| 4 | 41.7 |
| 5 | 42.8 |
| 6 | 43.9 |
| 7 | 45.0 |
| 8 | 46.1 |
| 9 | 47.2 |

| KEY: | CONTOUR NO. | TEMP. (°C) |
|---|---|---|
| | 1 | 38.4 |
| | 2 | 39.5 |
| | 3 | 40.6 |
| | 4 | 41.7 |
| | 5 | 42.8 |
| | 6 | 43.9 |
| | 7 | 45.0 |
| | 8 | 46.1 |
| | 9 | 47.2 |

| KEY: | CONTOUR NO. | TEMP. (°C) |
|---|---|---|
| | 1 | 38.4 |
| | 2 | 39.5 |
| | 3 | 40.6 |
| | 4 | 41.7 |
| | 5 | 42.8 |
| | 6 | 43.9 |
| | 7 | 45.0 |
| | 8 | 46.1 |
| | 9 | 47.2 |

DIVERGENT ULTRASOUND ARRAYS

This is a Continuation of application Ser. No. 936,246 filed on Dec. 1, 1986, now abandoned.

BACKGROUND OF THE INVENTION

The present invention relates to divergent ultrasound arrays of transducers adapted to treat medical conditions responsive to ultrasound such as physiotherapeutic conditions and the treatment of neoplastic tissues by ultrasound hyperthermia.

In physiotherapy it has been known to use an ultrasonic transducer in contact with the skin to treat various pain inducing conditions in the joints for example. The use of these ultrasound transducers of the convergent variety is limited because the transducer head must be in intimate contact with the skin, and in that the power output cannot be raised too far because local heating of the skin exceeds patient tolerence. Accordingly, only fairly low ultrasound intensities can be applied to affected parts; ultrasound treatments in depth are not possible.

Focused convergent arrays are also impractical because of the difficulties in providing an acoustic focus at an appropriate point having regard to the presence of bone etc., particularly with the added requirement that with most therapeutic conditions no invasive temperature sensors can be utilized.

Local hyperthermia, in which temperatures normally in the range between 42° and 46° C. are maintained for periods from a few minutes up to several hours in neoplastic tissue, has been found to be beneficial for the treatment of cancer in cases where the whole tumour can be properly heated and the surrounding normal tissues can be spared. Many methods of producing local hyperthermia in cancer patients have been suggested and tested. Recently treatment of superficial human neoplasms by local hyperthermia induced by ultrasound has been shown to be useful.

For ultrasonically-induced local hyperthermia, the elevation of temperature inside the target tissue is affected by the ultrasonic absorption, the blood perfusion rate, the thermal conductivity of the tissue, and the choice of transducer parameters. It has been shown that the temperature distribution produced by a single convergent focused ultrasonic beam is very sharp even in the steady-state situations where the thermal conduction and blood perfusion smooth it. Moreover, we have found that the treated volumes are usually not large enough for most of the clinical cases.

In commonly assigned U.S. patent application No. now U.S. Pat. No. 4,646,756, Watmough et al. have described an array of sonic transducers radially disposed about an axis, angled to direct sonic energy toward said axis at a point of acoustic focus remote therefrom, and temperature sensing means for association with the point of acoustic focus whereby one or more transducers are adapted for relative angular movement thereby to allow adjustment of the shape and/or position of the acoustic focus in response to an output from the temperature sensing means.

A system utilizing circulating warm water in conjunction with multiple convengent ultrasonic beams to achieve local hyperthermia has also been described in the above U.S. patent application. The disclosures of U.S. Pat. No. 4,646,756 are hereby incorporated by reference herein.

When a single steered, focussed ultrasonic beam is used, only a small portion of the tumour tissue is heated at one time, so the elevation of the temperature inside the tumour is completely dependent upon the averaging effect induced by thermal conduction and blood perfusion in tissue. The possibility of under-heating or overheating a certain portion of tissue exists as the blood perfusion rate will change during treatment because of vasodilation. Furthermore, lack of homogeneity in blood flow and inhomogeneity in ultrasonic absorption in the tumour will greatly affect the temperature distribution. Moreover, a single steered and focussed ultrasonic beam takes a longer time to heat up a whole tumour to a therapeutic temperature level, and also involves much higher instantaneous intensities.

The array in accord with U.S. Pat. application Ser. No. 544,820, although effective, requires in practice the provision of computer controlled stepping motors to alter the focal points of the movable transducer array in response to outputs from said temperature sensing means, and this adds to the complexity and cost of the device.

SUMMARY OF THE INVENTION

We have now found that excellent therapeutic results can be achieved by using a divergent ultrasonic field in conjunction with warm water circulating over the skin above the treatment area to achieve local hyperthermia. This has some advantages because water circulating at 43° C. raises local tissue temperature at a depth of 3 cm below the skin to 40° C. Thus the intensity of ultrasound required to produce therapeutic temperatures can be much reduced, with the benefit of minimizing any potential side-effects of the ultrasound. Moreover, divergent fields are able to cover a bigger treatment volume and spare the organs beneath the treated area because of the reductions in local intensity. Further the microprocessor/microcomputer control is relatively simple since it does not need to control stepping motors.

According to the present invention therefore there is provided an ultrasound hyperthermia unit including an ultrasound transducer assembly angled to direct sonic energy toward a target, characterised in that the array comprises a plurality of divergent transducers each directed to provide a treatment field about a central axis.

A temperature sensing means for operative association with the array, and adapted to provide an output signal indicative of temperature values adjacent a target tumour, may be provided when the unit is adapted for use in the treatment of neoplastic tissues. In this instance the arrangement is such that said output signal is utilised to control the power output of the array to achieve localised heating of the tumour tissues above viability.

In both the above foregoing instances (physiotherapeutic treatment and the treatment of neoplastic tissues) a liquid bath may be located between the array and the skin of a patient, said liquid bath being adapted to warm the superficial tissues. Optionally, the assembly may be provided with a transducer coaxial with the central support axis, and with a plurality of divergent transducers arranged radially about the central axis.

A system in accordance with this invention may comprise a warm-water circulating unit for contact with the skin of a patient, which forms a single unit with a transducer array, of preferably four or five divergent transducers. The bath may be formed in part of a flexible membrane so that it can change its shape in use to modify the distance between the array and the superficial tissues. One transducer may be a plane transducer and may be placed centrally with the other four or five transducers symmetrically placed around it, but inclined to it at an angle of, for example, 66.4° to the main axis of the central transducer.

In a preferred embodiment the tranducer array is formed of a support into which selected tranducers may be plugged as necessary. The assembly of the invention may also be provided with a liquid lens in association with each transducer to alter the ultrasound distribution for different treatments.

In a preferred embodiment the transducers may be interspersed with one or more imaging or temperature sensing transducers to allow the array to provide further information. One of the ultrasound transducers can, for example, also be used intermittently in a sensing role, or the additional transducer can be used in a pulsed or phased sensing mode.

The temperature sensing means may be a thermocouple or other sensing device adapted for positioning adjacent to or in the tumour tissue. This is preferably a linearly arranged sensor with a plurality of sensing positions along its length whereby a single needle insertion will provide all the required temperature information for microprocessor control.

Alternatively, non-invasive probes may be used such as microwave thermometers.

Additionally, the skin overlaid by the bath may have in contact therewith a liquid crystal device to indicate the temperature of the skin by colour changes.

The assembly of the invention may be controlled by a microprocessor which utilizes the temperature signals to control the power output thereof. This enables field contours, (i.e., isotherms) to be arranged to conform with non-symmetric tumour shapes. Further by this or other means the frequency of the ultrasound may be stepped up or down to harmonic higher harmonic or sub-harmonic frequencies to alter depth, and/or temperature distributions, since we have found that absorption coefficient depends on frequency. Further, square wave or sinusoidal signals may be selected to alter temperature distribution.

Simpler assemblies are usually required for use in physiotherapy. Generally, the temperature sensing means can be dispensed with, and the unit will operate without a water bath so long as the array is in intimate contact with the skin. However, a water bath enables the unit to be readily used on difficult body contours such as elbows and knees, and gentle warming of the skin in these areas assists treatment by reducing the amount of ultrasound required.

Because ultrasound is directed toward a source of pain from, for example, five different directions, higher intensities can be applied to a target joint, for example, without affecting patient tolerance. The use of divergent transducers allows large volumes of tissues to be treated without adversely affecting underlying sensitive tissues because the applied power decreases exponentially.

The invention will now be described by way of illustration only, with reference to the accompanying drawings which show:

FIG. 1: A top-view of an array with five transducers for use in physiotherapy or the treatment of neoplastic tissues.

FIG. 2: The side-view of an alternate array with five transducers in conjunction with a water bath, including a central planar imaging transducer.

FIG. 3: The geometry of the transducers array of FIGS. 1 and 2 in use.

FIG. 4: The iso(pressure)$^2$ curves with the increment of 12.5% of the peak value in an axial plane for the five divergent transducers array in water (Frequency=1.1 MHz, diameter of transducer=5 cm, radius of curvature=12.1 cm and the voltage fed into the central transducer is five times that fed into the other transducers).

FIG. 5a. The iso(pressure)$^2$ curves with the increment of 12.5% of the peak value in a transverse plane at z=15.6 cm for the five divergent transducers array in water (Same conditions as FIG. 4).

FIG. 5b: The field pattern registered on a piece of paper which was placed 15.6 cm away from the front edge of the array (The method of experiment is described in the text.)

FIG. 5c: The pressure-squared distribution along the x-axis in FIG. (5b) (All parameters are the same as that in FIG. (5a) except that the interval between each data point is about $\frac{1}{8}$ wavelength of the ultrasound beams).

FIG. 6a: The iso(pressure)$^2$ curves with the increment of 12.5% of the peak value in a transverse plane at z=5.6 cm for the five transducers array in water (Same conditions as FIG. 4).

FIG. 6b: The field pattern registered on a piece of paper which was placed 5.6 cm away from the front edge of the array.

FIG. 6c: The pressure-squared distribution along the x-axis in FIG. (6b).

FIG. 7: The model used in the calculation of temperature distributions: a volume of 10*10*10 cm$^3$ of tissue has a tumour volume of 3*3*3 cm$^3$ which is situated at 1 cm beneath the skin.

FIG. 8: The temperature distribution in a longitudinal plane calculated from the 3-D simulation model.

FIG. 9: The temperature distribution in the transverse plane (2 cm deep from the skin) calculated from the simulation model.

FIG. 10: The temperature distribution in the transverse plane (2 cm deep from the skin) calculated from the simulation model.

FIG. 10: The temperature distribution in the transverse plane (3 cm deep from the skin) calculated from the simulation model.

FIG. 11: The temperature distribution in the transverse plane (4 cm deep from the skin) calculated from the simulation model.

FIG. 12: The temperature distribution in the transverse plane (5 cm deep from the skin) calculated from the simulation model.

FIG. 13: The axial temperature distribution calculated from our computer model versus depth after 2.5 minutes of sonication under the assumption that the blood perfusion rate is 10% (□) and 50% (◇) of the peripheral respectively.

FIG. 14: The temperature distribution in a longitudinal plane calculated from the simulation model under the assumption that the blood flow is normal tissue is 9.6 ml/Kg/sec. (The other conditions are the same as that in FIG. 8.)

DETAILED DESCRIPTION OF PREFERRED EMBODIMENTS

The above figures show the theoretical calculation of the field patterns produced by an array of transducers comprising four equally spaced transducers disposed about a central transducer. The equally spaced transducers are arrayed at a fixed angle to the central axis. A computer simulation model to simulate the effects of blood flow, thermal conduction, ultrasonic absorption in tissues, skin temperature and different power settings of the transducers on the temperature distribution inside the tissue during local hyperthermia is also shown. The method is applicable to the prediction of temperature distributions in tissue for different numbers of transducers and different geometrical configurations.

Figure 1:
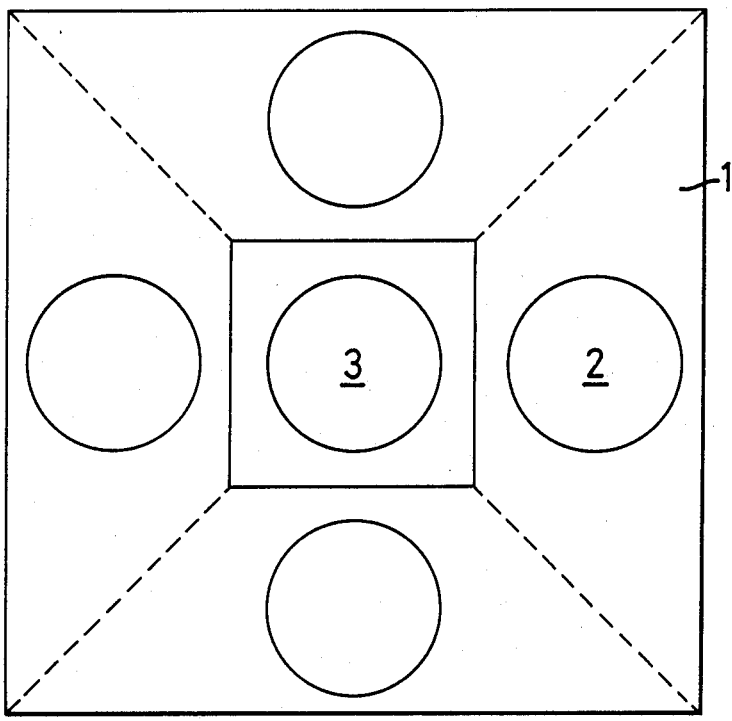
Figure 2:
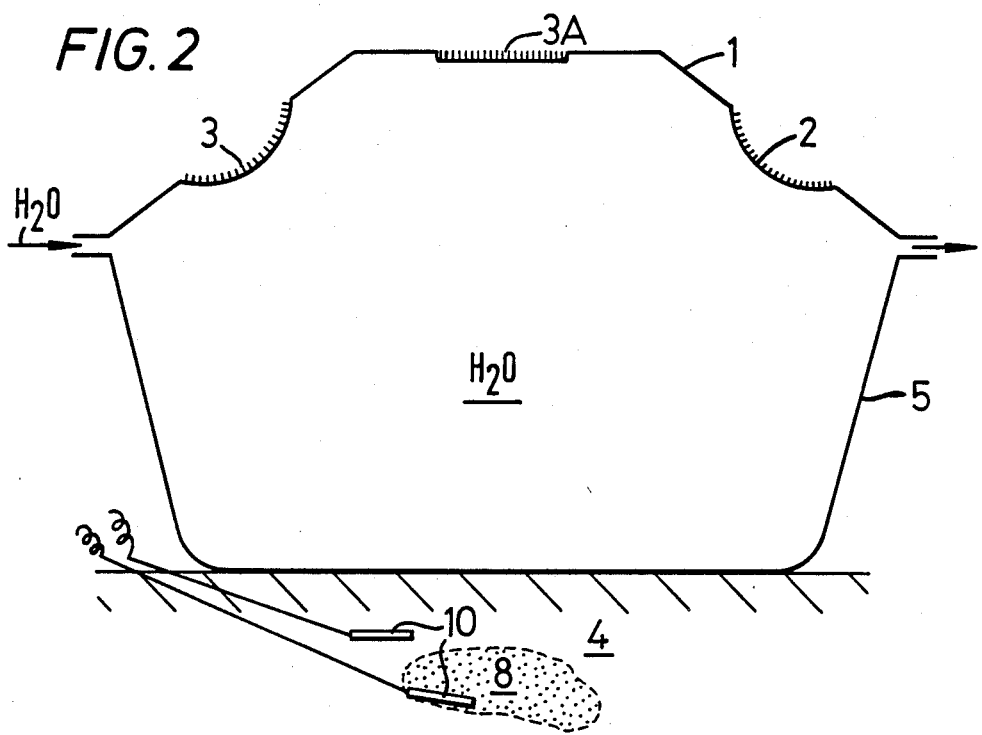
Figure 3:
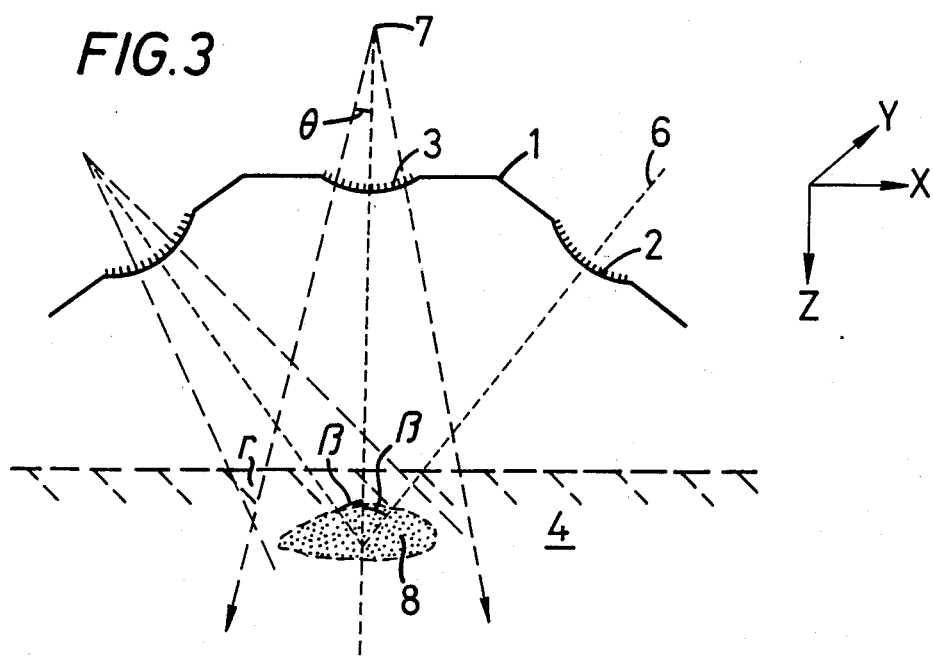
Figure 5A:
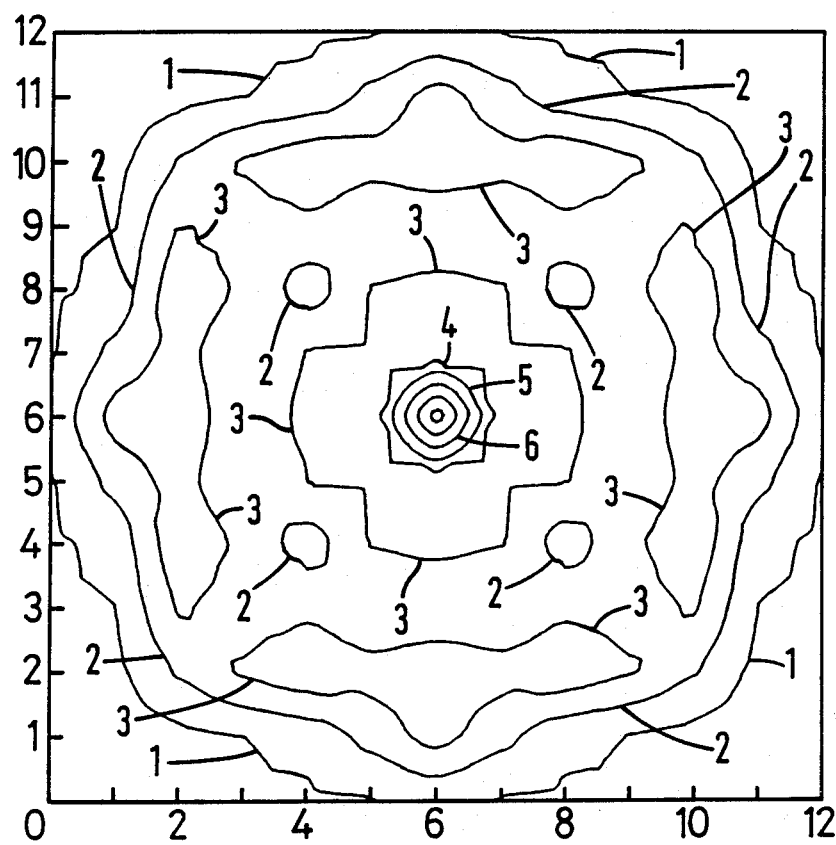
Figure 5B:
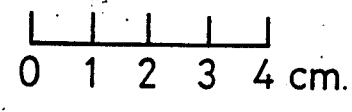
Figure 5C:
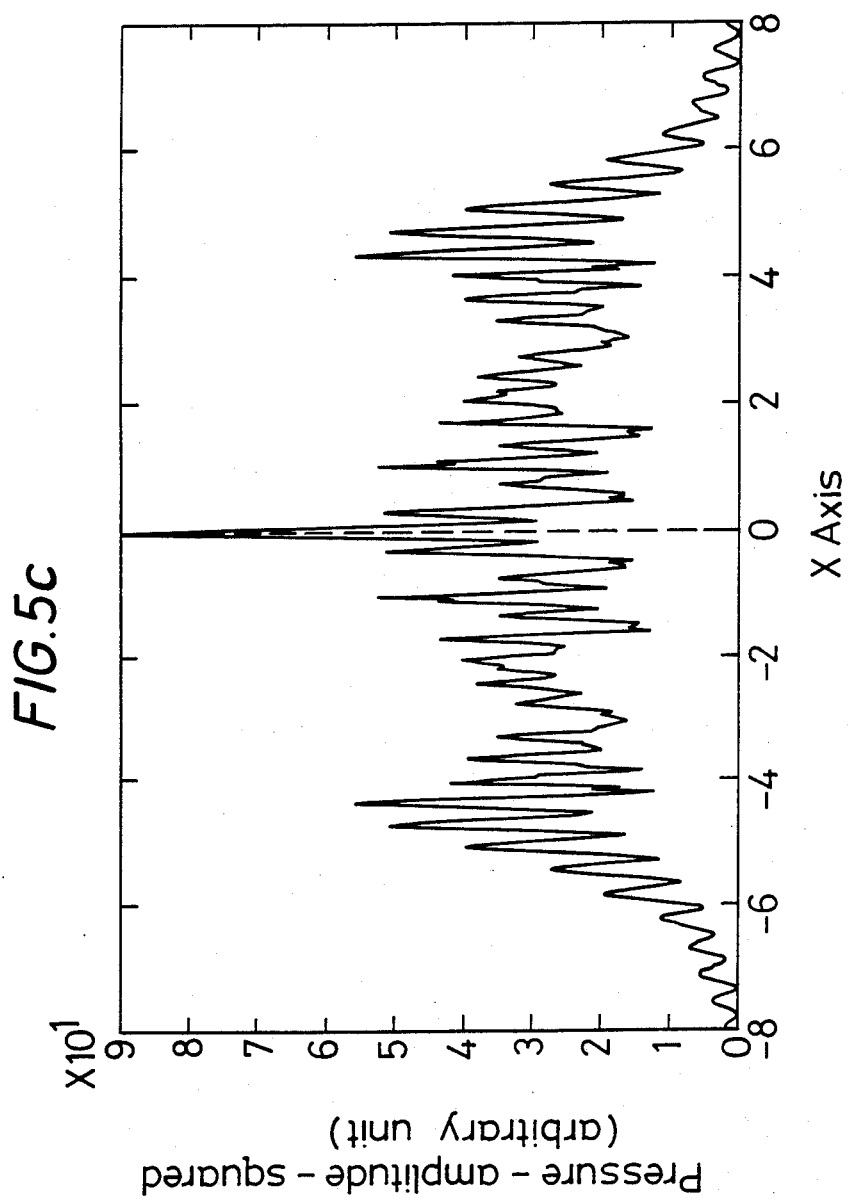
Figure 6A:
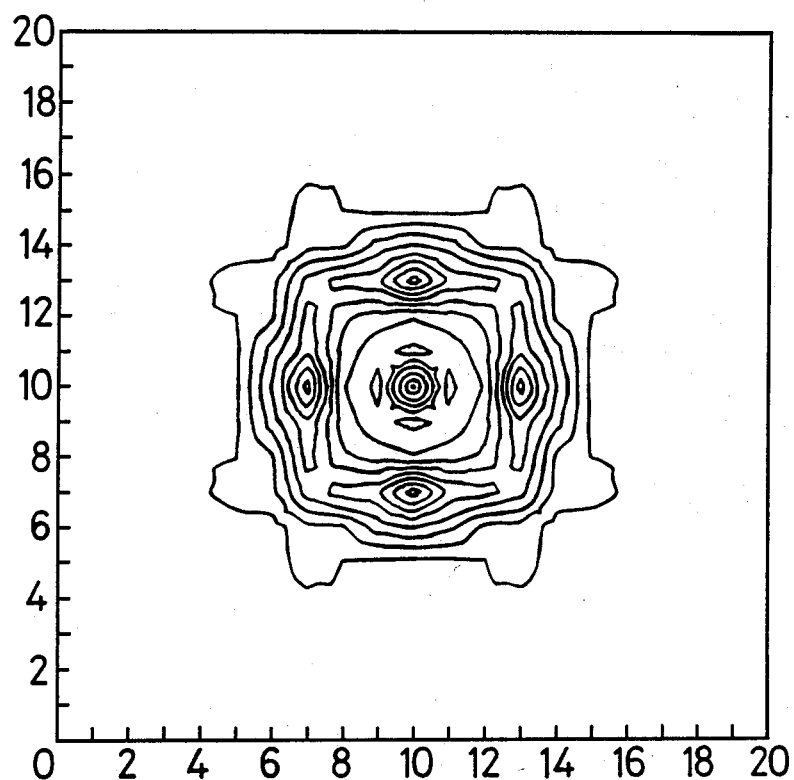
Figure 6B:
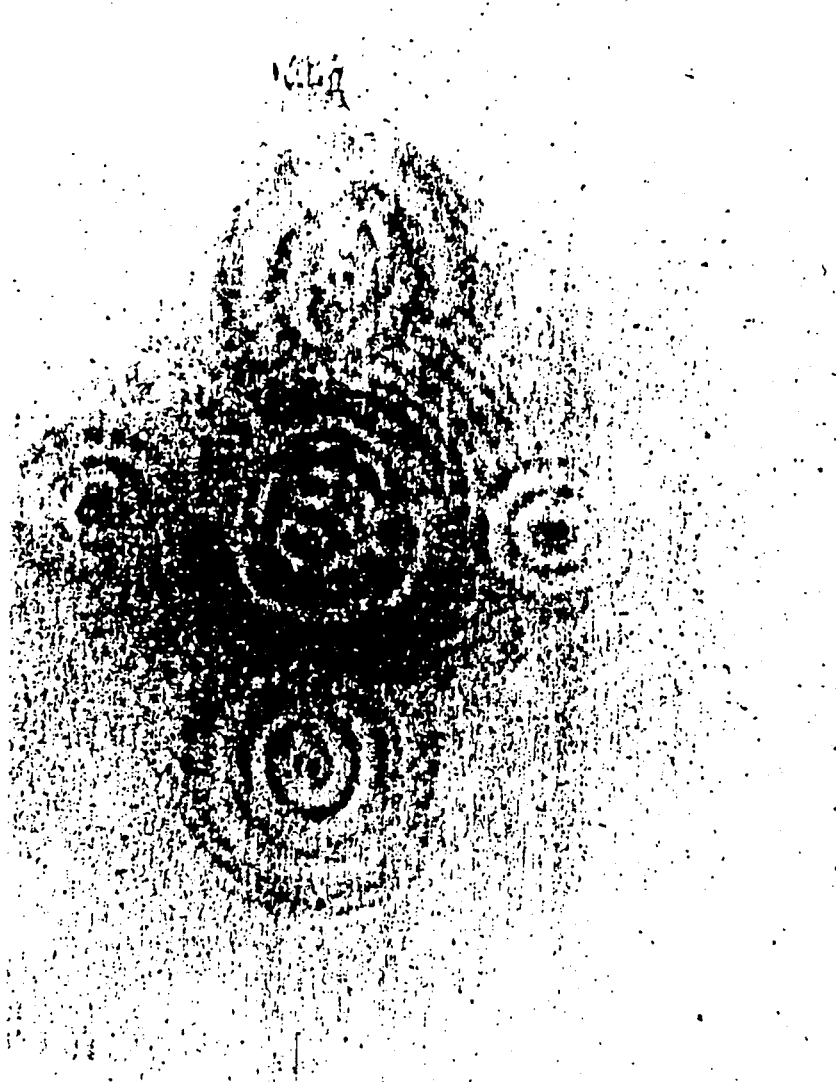
Figure 6C:
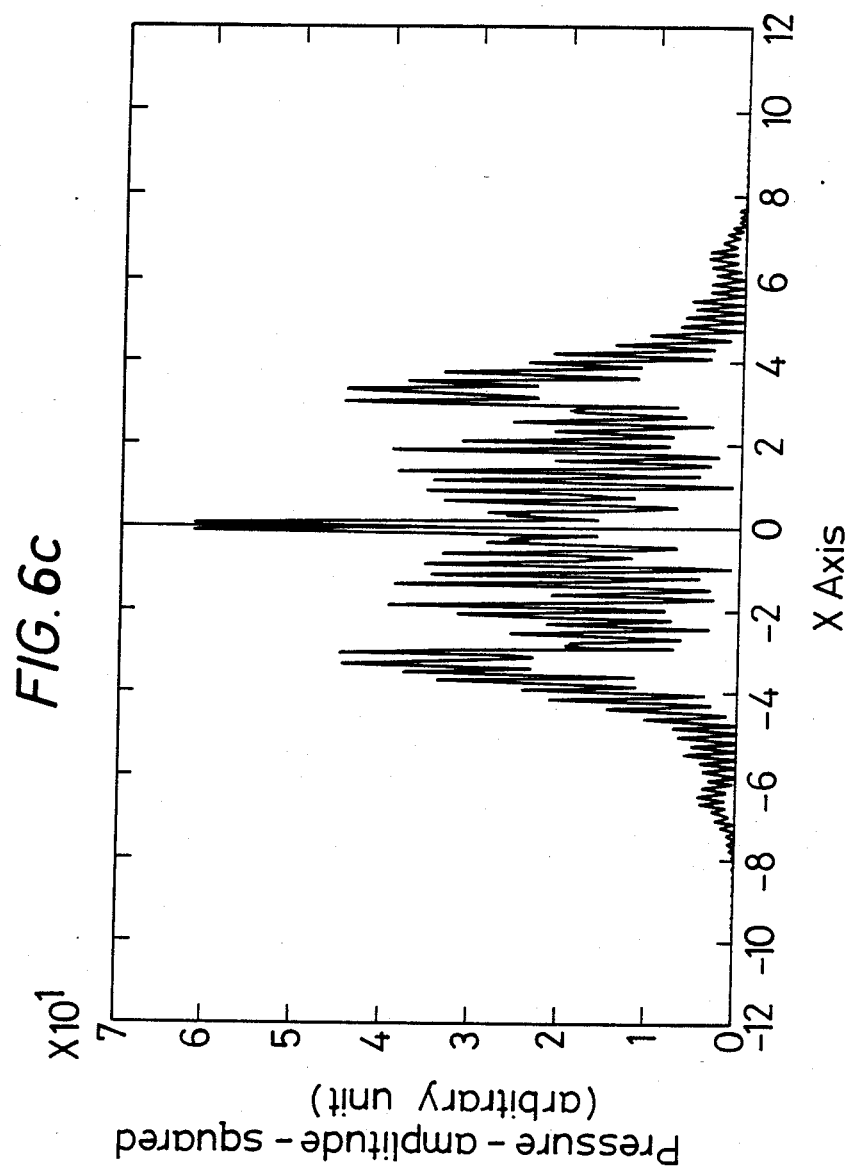

With particular reference and FIGS. 1 to 3 a substantially rectangular transducer array 1 provides a frame for the support of a plurality of radially spaced divergent transducers 2 in equally spaced relation. FIG. 2 shows an alternate array including a planar imaging transducer 3A which is concentric with the central axis of the central axis of the transducer array. The angles of the transducers and their configuration are apparent from FIGS. 1-3, from which it will be noted that each heating transducer is a divergent transducer, and that although each transducer is directed toward a common focal point when the central axes of each transducer are considered, each is capable only of providing a divergent sonic field, over a certain predetermined area wherein a target lies. This target may be a knee joint or a neoplastic tissue.

The central transducer 3 is provided about the central axis of the array and may, if desired, be adapted to perform special functions.

With reference to FIG. 2, the array and water bath assembly, in accordance with the present invention is shown in strictly diagrammatic form. Water entering the water bath 5 from the left hand side of the FIG. 2 exits from the water bath and transducer assembly to the right hand side of the FIG. 2 as shown in the drawings. The water maintains the skin temperature at a desired temperature, for example when treating neoplastic tissues about 42° C. in the absence of any power from the transducers. The skin 4 overlying a target, for example a tumour shown diagrammatically at 8, has a plurality of sensors 10 inserted therein in juxtaposition with, and into, the tumour 8. Outputs from the sensors 10 are fed to a computer which can be utilized to control the power of each transducer separately. A suitable system for controlling the power of the ultrasonic transducers, including a computer or microprocessor and temperature sensing means adjacent a tumour site, is disclosed in U.S. Pat. No. 4,646,756; see FIGS. 2 and 7. The sensers 10 are not required for physiotherapy since the power output can be controlled on an empirical basis.

The transducer array is operatively connected to the water bath such that the induced sound passes through the water bath into the patient with a minimum of power loss. This ensures that a minimum level of ultrasonic power is required to achieve maximum heating of the target area.

As is shown in FIG. 3 a central axis 7 is defined by the central transducer 3, whereas a peripheral axis 6 of each adjacent transducer has a point of conjunction with the central axis 7. This is not, however, an acoustic focus since the acoustic transducers are of the divergent type.

The unit of FIGS. 1 to 3 may be adapted for use physiotherapeutically in the following conditions:
  Trauma to tibia
  Painful arc syndrome
  Medial meniscus lesion
  Degenerative changes
  Pain—thoracic vertebrae
  Tenderness over rhomboid
  Bruised perineum and haemorrhoids
  Haematoma of line of episiotomy
  Bruised oedematous perineum.
  Rotator cuff lesion
  Contraceptive and induration of delto-pectoral flap
  Torn attachment—abdominal muscles (sports injury)
  Medical ligament—knee
  Chronic strain of abdominal muscles
  Haematoma soleus
  Plated ankle
  Biceps femoris strain
  Bicepital haematoma
  Acute tear ligament; med. ligament (knee)
  Pain paraesthesia distribution T10
  Laceration dorsum of hand
  Sacro-iliac strain
  Ligament injury—ankle
  Traumatic injuries: foot, thumb
  Dislocation of shoulder
  Contusion—shoulder joint (MS)
  Sprain—ankle
  Pre-tibial inflammation
  Muscle contusion
  Injury to acromio clavicular joint
  Back strain
  Swelling and bruising: tibia, ankle
  Effusion and bruising of knee
  Herpes Zoster
  Haematoma above L. lat. malleolus
  Undisplaced fracture-styloid-process radius
  Soft tissue injury
  Effusion R. pre-patellar bursae
  Acute torticollis
  Painful Trapezius
  Strain-Trapezius and Rhomboids
  Epicondylitis
  Vastus muscle strain
  Pain following Colles fracture
  Strained hamstrings
  Tendon repair: thumb
  Divided flexor tendons
  Tenosynovitis extensors: wrist
  Gastrocnemius
  Referred arm pain
  Adhesions following road traffic accident-knee
  Chondromalacia—knee
  Adherent scar—(swollen fingers)

Theory (A) Calculation of the field pattern produced by the array of five divergent transducers In linear acoustics the sound waves caused by the radial motion of a sphere are governed by the first order wave equation $$\nabla^2 p + k^2 p = 0 \qquad \text{Eq1}$$

when we consider only harmonic time variations for the acoustic pressure p (where $k = w/c$, w is the angular frequency, c the sound speed). If we take a particular case of a polar cap whose surface vibrates with a velocity $u_o\exp(-iwt)$, the half-angle subtended by the curved surface at the centre of curvature is $\theta_o$, and the radius of curvature of the polar cap is b, then the solution of the differential equation (Eq1) can be expressed as $$p(r,\theta,t) = \frac{\rho c(1-\cos\theta_o)u_o\exp(-iwt)}{4i} \sum_{n=0}^{\infty} \frac{P_{n-1}(\cos\theta_o) - P_{n+1}(\cos\theta_o)}{h'_n(kb)} h_n(kr)P_n(\cos\theta) \quad \text{Eq(2)}$$

where P is the density of the medium in which ultrasound is propagating, P stands for Legendre function, h stands for spherical Hankel function and the prime in the denominator indicates differentiation with respect to the argument kb. This series has been shown to be uniformly convergent in any region $r>b$ (Wilcox 1956).

The ultrasonic field produced by a divergent transducer shaped like a polar cap can be described by Eq(2). When an array of five transducers is considered, the resultant pressure at the point (r, $\theta$) is the vector sum of the individual pressures at that point produced by each transducer. Although the particle velocity near a vibrating surface is not in phase with the pressure, the particle velocity will be in the radial direction and in phase with the pressure when it is far from the vibrating surface (Morse etal, 1968). Hence the resultant intensity will be proportional to the square of the resultant pressure when kr is very large. Mathematically, it is expressed as follows:

$$I \alpha [p(\text{total})]^2 = \left| \sum_{j=1}^{5} P_j \right|^2 \quad \text{Eq(3)}$$

A computational program has been developed to calculate the intensity distribution generated by the array of five divergent transducers where each transducer is driven with the same sinusoidal frequency but with different voltage.

(B) Computer simulation model of temperature distribution in tissue during local hyperthermia induced by our five transducers array The general heat conduction equation $$\rho s \frac{\partial T}{\partial t} - k\left(\frac{\partial^2 T}{\partial x^2} + \frac{\partial^8 T}{\partial y^2} + \frac{\partial^2 T}{\partial z^3}\right) = \quad \text{Eq(4)}$$

$$H(x,y,z) - C(x,y,z,T)$$

has previously been employed to simulate the temperature distribution in tissue during local hyperthermia induced by ultrasound (Hynynen etal 1981) Here P is the density of the tissue, S the specific heat, T tissue temperature, t time, k the thermal conductivity of the tissue, xyz space coordinates, H the rate at which heat is being generated by ultrasound in the element (x, y, z) per unit volume and C the cooling function induced by blood perfusion in tissues.

Many standard methods have been employed to solve the general heat conduction equation. Finite-difference approximation is one of the numerical approaches (e.g.: Chapman 1974; Hildebrand 1968). For explicit finite-difference formulation, Eq(3) can be transformed into $$T(x,y,z,t+1) = \lambda [T(x-1,y,z,t) + T(x+1,y,z,t) + \quad \text{Eq(5)}$$

-continued $$T(x,y-1,z,t) + T(x,y+1,z,t) + T(x,y,z-1,t) +$$

$$T(x,y,z+1,t) - 6T(x,y,z,t)] + T(x,y,z,t) + (\Delta t)/(\rho s) [H(x,y,z) -$$

$$C(x,y,z,T)]$$

under the assumption that the spatial increments ($\Delta x$, $\Delta y$, $\Delta z$) are equal and $\lambda$ represents $k(\Delta t)/(\rho s \Delta x^2)$ which is a dimensionless parameter. In order to satisfy stability and convergence criteria, $\lambda$ must be taken to have any positive value less than 1/6 (Chapman 1974).

It is accepted that the blood perfusion rate in most tumours is usually lower than that in the surrounding normal tissues, but the blood perfusion rate at the advancing front (tumour periphery) is often much higher. Therefore, we have developed a computer simulation program to simulate the effect of perfusion on temperature distribution during hyperthermia treatment generated by our 5-element transducer array. Also we take account of the thermal conduction and ultrasonic absorption.

COMPUTER PREDICTIONS (A) intensity distribution in water

In the disclosed embodiment of the present invention there are five transducers in the array. The radius of curvature of each transducer is 12.1 cm and the half-angle subtended by the curved surface at the centre of curvature is 11.9°. The main axis of each transducer is inclined 23.6° with the main axis of the central transducer (FIG. 3). Each transducer in the array can be fed with a different voltage in order to achieve different intensity distributions and hence correspondingly different temperature distributions in tissue. Empirically, in the first instance, the voltage fed into the central transducer is five times higher than that fed into the four outer transducers. The (acoustic pressure amplitude)$^2$ distribution in a longitudinal plane (XZ-plane) is calculated by using Eq (2)and(3) and the result is presented in FIG. 4. In addition, the (acoustic pressure amplitude)$^2$ distributions in the transverse plane at 5.6 cm and 15.6 cm away from the edge of the transducer unit are presented in FIG. (5a) and FIG. (6a). These show that the acoustic intensity diminishes rapidly with distance along the axis and varies symmetrically about the XZ- and YZ-planes. The acoustic pressure-amplitude-squared distributions also show that use can be made of the intensity distribution between z=10 and 20 cm for hyperthermia because in that region a large tissue volume will be heated with reasonable uniformity. Moreover, the surrounding tissue and the organs beneath the treated area will be spared because the ultrasonic intensity diminishes very rapidly with distance.

The ultrasonic field patterns were visualized as follows: The transducer array was immersed in a tank of water with a few drops of methylene blue dye added. Pieces of white paper were sequentially placed at different positions in the path of the ultrasonic beam. The dye particles move under the influence of the ultrasonic field and are trapped in the paper, so that a coloured pattern corresponding to the field distribution is produced on the paper.

The pattern registered at 15.2 cm away from the array, obtained in this way, is shown in FIG. (5b). The shape of the pattern is consistent with the computer simulation. However, FIG. (5b) shows a clear interference pattern which is produced by the interference between the five ultrasound beams. FIG. (5a) does not show this pattern. This is because the data points in the mesh for producing FIG. (5a) are relatively sparse (i.e.: the separation between each data point is greater than the wavelength of the ultrasound beams), so that the interference pattern does not appear in FIG. (5a). The data point separation has to be large to ensure realistic computing time. If the separation between each data point in the mesh is reduced to a value which is smaller than the wavelength, our simulation model will show the detail of the interference pattern.

In fact, the pressure-amplitude-squared distribution along the x-axis with an interval of 0.04 cm between each data point is plotted in FIG. (5c). The interference pattern in FIG. (5b) and the result of simulation shown in FIG. (5c) are consistent. Similarly, FIG. (6c) shows the pressure-amplitude-squared distribution along the x-axis in FIG. (6b) which shows the field distribution pattern at 5.6 cm away from the front face of the transducer unit.

(B) Temperature distribution in tissue

The actual elevation of temperature in tissue during local hyperthermia can be affected by many factors; different blood perfusion rate in tumour and in normal tissues, thermal conductivity of tissue, and ultrasonic absorption. The overall parameters of thermoregulatory response in the human body are very complicated, but the major factor is the cooling function in local hyperthermia which can be mainly attributed to the blood flow in tissue. A warm-water bath, which is maintained at a constant temperature, say 42° C., was placed on the patient's skin just above the treated area in order to reduce the ultrasonic power and minimize the heat loss through skin in the course of local hyperthermia treatment of superficial neoplasm.

Figure 7:
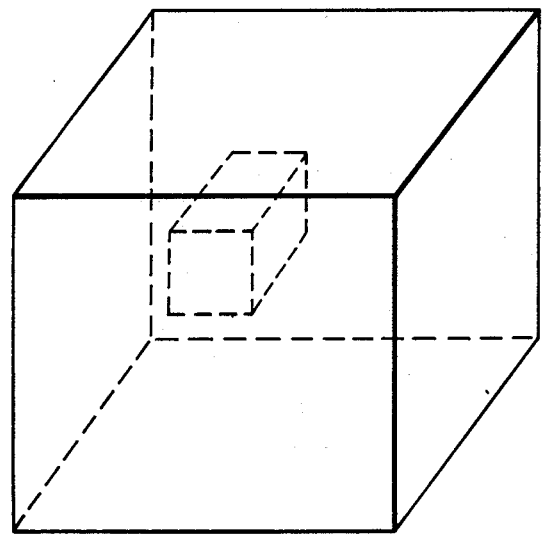
Figure 8:
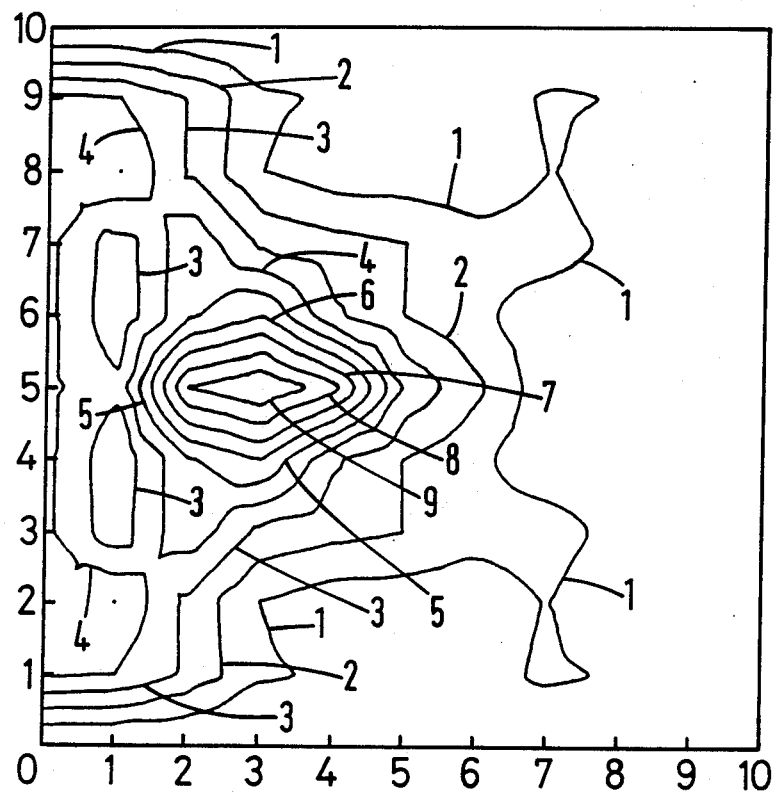
Figure 9:
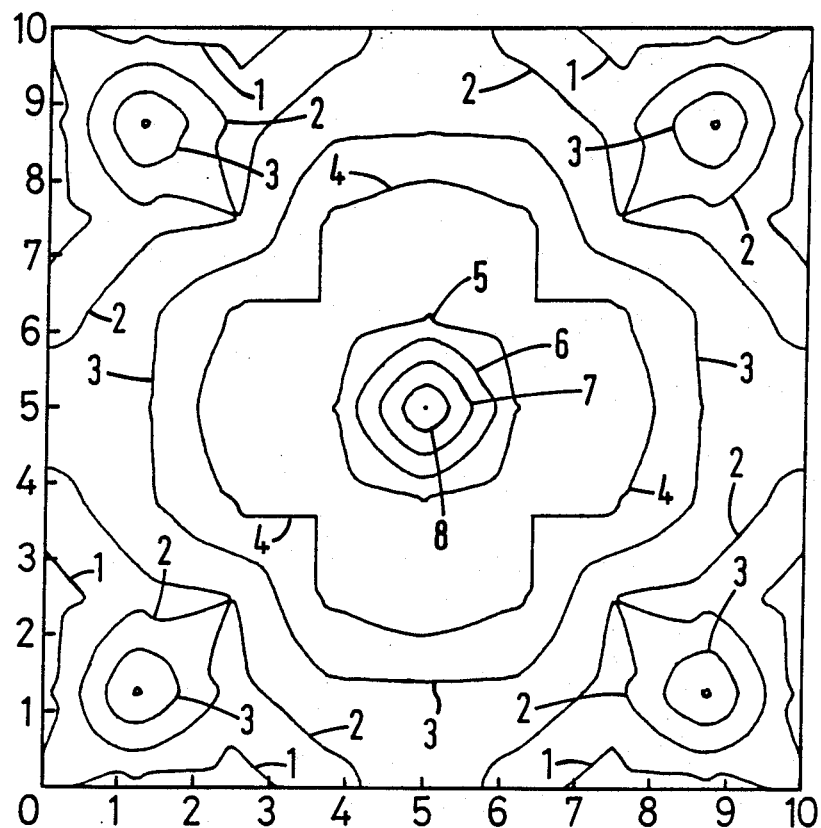
Figure 10:
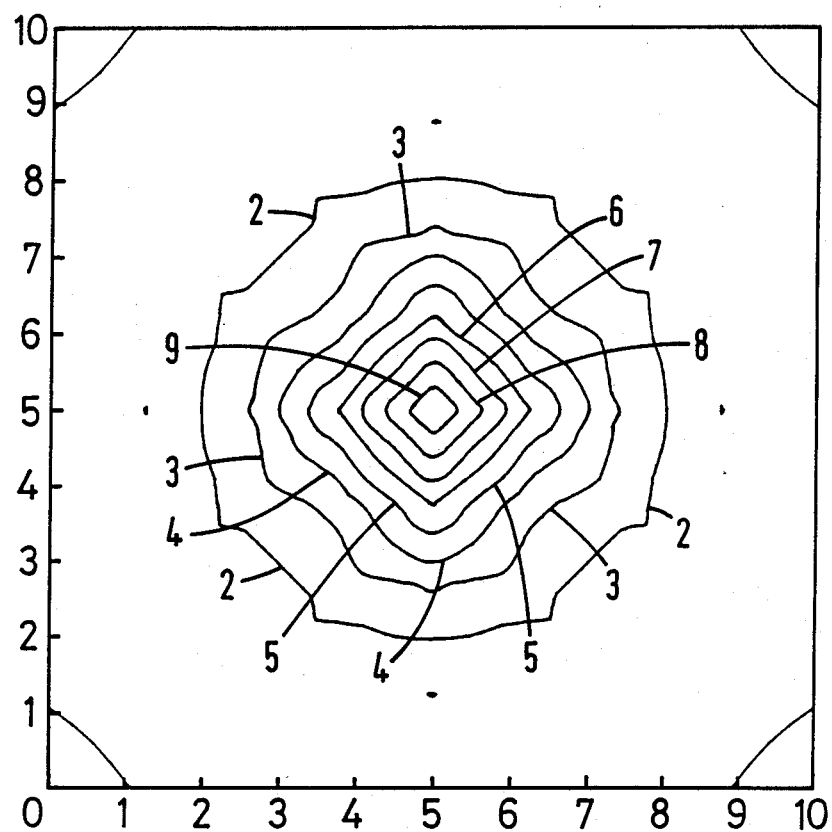
Figure 11:
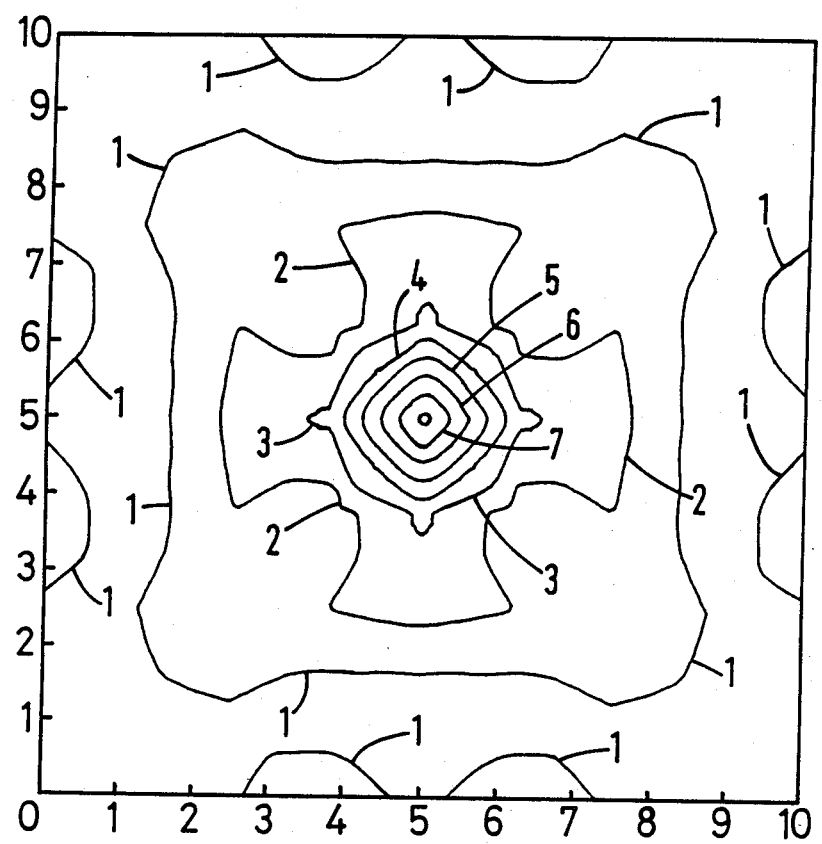
Figure 12:
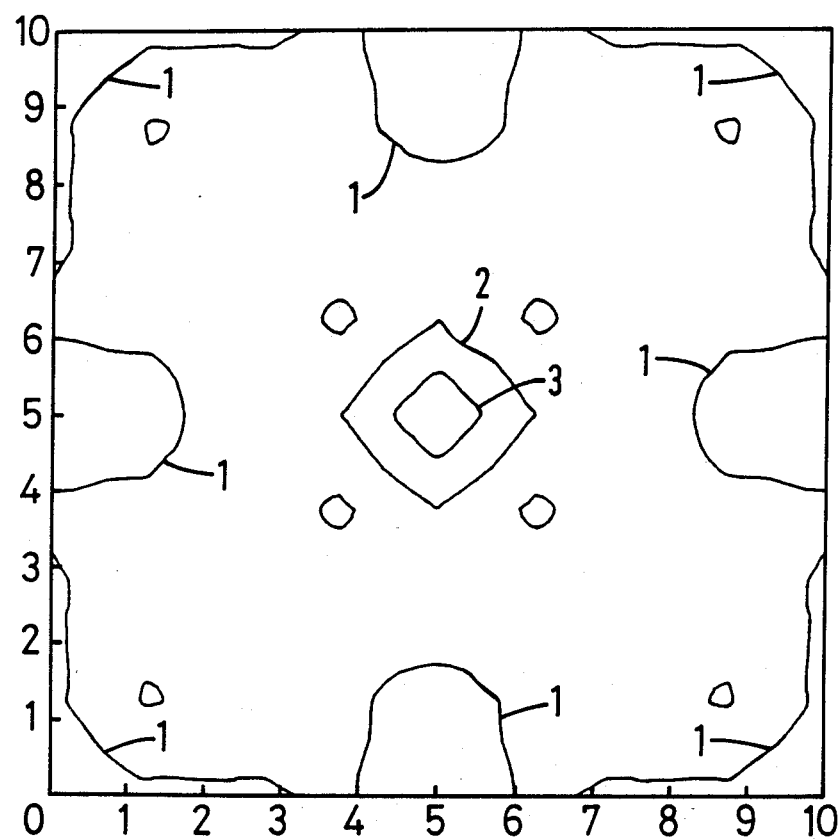

In the 3-D computational simulation model we consider the following conditions: the temperature distribution in a cube $10*10*10$ cm$^3$ is located at 1 cm below the skin (see FIG. 7). The blood perfusion rate inside the tumour is assumed to be only 10% of that in the peripheral tissues. The blood perfusion rate in the tumour's periphery and in normal tissue is 2.3 ml/kg/sec and 0.5 ml/kg/sec respectively. The thermal conductivity of the tissue is 0.44 W/M/K, ultrasonic attenuation is 8 Np/M and the skin temperature is maintained at 42° C. (by placing a warm-water bath on the skin). The spatial temporal average of the ultrasonic intensity in degassed water at $z=13$ cm is 3.8 W/sq.cm. The patient's skin is 10 cm away from the central transducer. The results of computer simulation are shown in FIGS. 8–12. FIG. 8 shows the temperature distribution in tissue along a longitudinal plane (XZ-plane) after 2 minutes of sonication. It indicates that the maximum temperature 48.4° C. is about 2 cm below the skin and the iso-temperature curve of 42.8° C. covers an ellipsoidal volume with a maximum diameter of about 3 cm and 4 cm long, (i.e., about 37.7 cm$^3$). All the tissue at 5 cm below the skin is spared. FIG. 9, 10, 11 and 12 show the temperature distribution in the transverse plane (XY-plane) at the depth of 2, 3, 4 and 5 cm below the skin respectively. They further support the view that the overlapping divergent fields produce an acceptable heating pattern during hyperthermia treatment of a superficial neoplasm.

Figure 13:
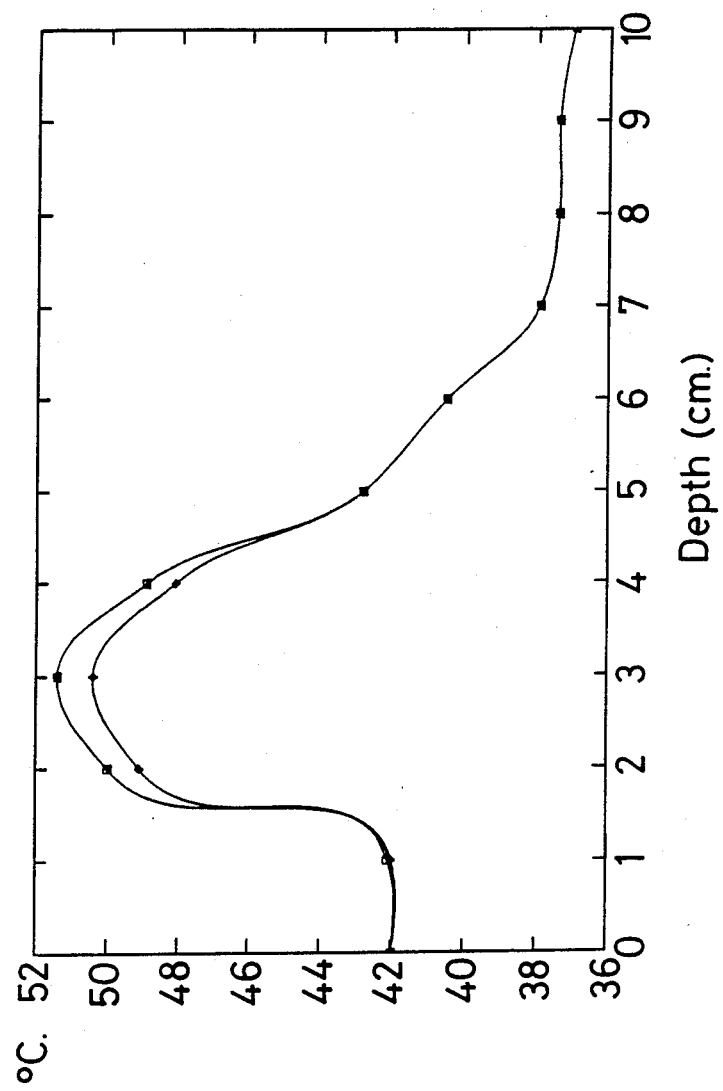

The blood perfusion rate can affect the temperature distribution. Where the blood perfusion rate in the tumour is 10% and 50% of the peripheral blood flow respectively, and the blood flow in normal tissue is unchanged, the axial temperature distribution in tissue as a function of depth at different times is plotted in FIG. 13. Results show that the maximum temperature will be reduced by about 1° C. after 2.5 minutes of sonication if the blood perfusion rate in the tumour is increased from 10% to 50% of the peripheral blood perfusion rate.

Furthermore, the blood perfusion rate in the surrounding normal tissue can also affect the temperature distribution. Where the blood perfusion rate in the tumour is 10% and 50% of the peripheral blood flow respectively, and the blood flow in normal tissue is unchanged, the axial temperature distribution in tissue as a function of depth at different times is plotted in FIG. 13. Results show that the maximum temperature will be reduced by about 1° C. after 2.5 minutes of sonication if the blood perfusion rate in the tumour is increased from 10% to 50% of the peripheral blood perfusion rate.

Figure 14:
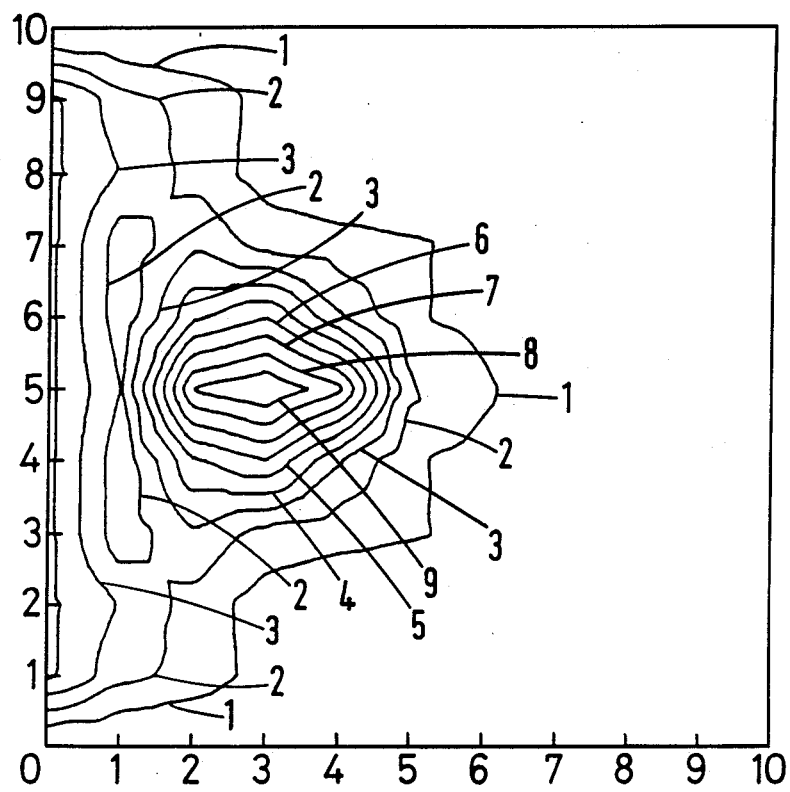

Furthermore, the blood perfusion rate in the surrounding normal tissue can also affect the temperature distribution. Where the blood perfusion rate in the normal tissue is 9.6 ml/Kg/sec (e.g., in normal liver) and the blood perfusion rate in the tumour is still 10% of the peripheral, the temperature distribution along a longitudinal plane is shown in FIG. 14. It shows a slightly different temperature distribution as compared to that in FIG. 8. The iso-temperature curve of 42.8° C. still covers about the same volume but the temperature elevation outside the tumour volume is reduced.

Blood flow and Temperature Distribution

Both the $^{133}$Xe clearance method used for a quantitative measurement of perfusion in superficial tumours and the measurement of scattering of ultrasound by blood flowing in breast cancers, show that most superficial tumours have a considerably lower flood flow than that in the surrounding normal tissue. Frequently, a tumour has a well perfused advancing front and a necrotic centre. This inhomogeneity in blood flow in tumours makes it difficult for a focused convergent transducer, either fixed in position or moving around the treatment field, to achieve a uniform temperature distribution in the whole tumour simultaneously. Moreover, in practice, it is not easy to concentrate the energy very accurately in the treatment zone and thus inhomogeneous temperature distributions must be accepted. This means that after the treatment some of the cells in the growing zone may still be viable, so that combination of chemotherapy or radiotherapy with hyperthermia is essential.

From the computer simulation calculation the 5-element hyperthermia unit described here can cover a superficial tumour volume of about 38 cm$^3$. Larger arrays can cover from 100 to 200 cm$^3$. If it is assumed that the blood perfusion rate in a tumour is only 10% of that at the periphery, the temperature gradient inside the tumour will be less than 2.7° C. per cm with the temperature maximum 48.4° C. at the necrotic centre after about 2 minutes of sonication. The temperature distribution is fairly uniform. The temperature of the tissue outside the tumour and the tissue at over 5 cm depth from the skin are below the therapeutic temperature level, and thus normal tissues are spared.

Temperature distributions inside tissue will be affected by the ultrasound intensity distribution. Where the central transducer in the array is fed with a voltage which is five times higher than that fed into the other transducers, the results of the simulation show that the shape of the treatment volume will be ellipsoidal. However, different treatment patterns will be produced to suit different clinical cases by adusting the ratio of voltages to and powers from each transducer. This is controlled by a temperature sensing element, or elements positioned in or about the tumour tissue.

Accurate measurement of temperature distribution inside the treatment volume is important for successful hyperthermia treatment and requires an array of thermocouples for example to be inserted into the tumour. See, for example, U.S. Pat. No. 4,646,756, at FIG. 7 and accompanying text.

Use of Warm-Water Bath

The use of a warm-water bath over the treatment field has several advantages: (1) It maintains a constant surface temperature to minimize any fluctuation caused by the physical environment. (2) It reduces the radiative heat loss through the tumour surface. (3) It acts as an ultrasound coupling. (4) It reduces the temperature gradient between the skin and the superficial tumour during local hyperthermia.

Thus, the total ultrasonic power required can be reduced but the therapeutic temperature level can still be maintained. Reducing ultrasonic power is beneficial to the patient because any actual or potential side-effects induced by ultrasound will be minimized. However, the warm-water bath itself cannot achieve a therapeutic effect even for superficial neoplasms because the heat penetration is not deep enough to treat a neoplasm and the hottest portion is then on the skin. When the divergent-transducer array is used in conjunction with the warm-water bath, it generates a uniform heating pattern suitable for treating superficial tumours lying between 0.5 cm and 4 cm below the skin.

In conclusion, according to the calculations of the ultrasonic fields generated by the five divergent transducers array and the computer simulation model of the temperature distribution inside tumours, the hyperthermia unit of the invention produces a relatively uniform heating pattern and is able to treat bigger tumour volumes and spare the surrounding normal tissues. Thus the unit is particularly suitable for treating superficial tumours lying at between 0.5 cm and 4 cm depth below the skin.

We claim:

1. An ultrasound hyperthermia unit including an ultrasound transducer assembly which directs ultrasonic energy toward a target disposed at a predetermined target location with respect to said assembly,
   wherein the assembly comprises a plurality of ultrasound transducers which are divergent in the near field because of their shape and arranged radially of a central axis, and thereby provide a treatment area which includes said target location about said central axis and adjacent said transducers in the near field.

2. A unit according to claim 1, further comprising means containing a liquid bath of an ultrasound-transmitting liquid adapted to be located between the assembly and the skin of a patient in said treatment area, said liquid bath being adapted to warm superficial tissues of such patient which are receiving said ultrasonic energy.

3. A unit according to claim 2, further comprising temperature sensing means for operative association with the assembly, and adapted to provide an output signal indicative of temperature values at and adjacent the target, an output signal being utilized to control the ultrasonic power output of the transducers.

4. A unit according to claim 2, wherein said means containing said liquid bath comprises a flexible membrane enclosing said liquid bath, whereby the bath can change its shape to modify the distance between the assembly and said superficial tissues of such patient.

5. A unit according to claim 1, wherein the assembly has a further transducer coaxial with the central axis.

6. A unit according to claim 5, wherein said divergent transducers are interspersed with at least one imaging transducer.

7. A unit according to claim 6, wherein said one or more imaging transducers are utilizable intermittently for imaging of said target area.

8. A unit according to claim 6, wherein said at least one imaging transducer is a plane non-divergent transducer arranged centrally of said divergent transducers.

9. A unit according to claim 8, wherein said divergent transducers are directed at an angle of substantially 66.4° with respect to the central axis of said transducer assembly.

10. A unit according to claim 1, further comprising means for the control of an ultrasound frequency of each said transducer, whereby harmonic, sub-harmonic or higher-harmonic frequencies can be selected as a control function for such transducer to alter treatment depth characteristics of the unit.

11. A unit according to claim 1, further comprising a liquid lens associated with each transducer to vary the focal volume of the treatment area.

12. In a method for physiotherapeutic treatment of tissue which comprises directing ultrasonic energy toward a target tissue, an improvement which comprises directing said ultrasonic energy from a transducer or transducers to treat the target tissue with ultrasonic energy which is divergent in the near field.

13. A method according to claim 12 which comprises inducing local hyperthermia at 40° C. to 45° C. in said target tissue.

14. The method of claim 12, wherein the transducers are radially arranged about a central axis and wherein one or more transducers are utilized in an imaging mode while the power to the other transducers which are not so utilized is switched off.

15. The method of claim 12, wherein harmonic or sub-harmonic or higher harmonic frequencies of each said ultrasonic transducer are selected for each said transducer to alter the treatment depth in response to the temperature sensed in or around the neoplastic tissue.

16. A method according to claim 12, wherein each said transducer has an outwardly convex curvature.

17. A method according to claim 16, wherein each said transducer has a spherical surface.

18. A method according to claim 16, wherein each said transducer is shaped like a polar cap.

19. In a method for the treatment of neoplastic tissue which comprises sensing the temperature within and about the neoplastic tissue and providing signals indicative of said temperature to a microprocessor, controlling an ultrasound transducer with said microprocessor to generate ultrasonic energy to induce local hyperthermia at about 40° C. to 45° C. at and adjacent said neoplastic tissue, by directing an array of ultrasonic energy toward the neoplastic tissue;

the improvement which comprises directing said ultrasonic energy from a transducer or transducers which are divergent in the near field because of their shape to raise the temperature of the neoplastic tissue above viability in a treatment area adjacent each of said transducers in the near field.

20. A method according to claim 19, wherein each said transducer has an outwardly convex curvature.

21. A method according to claim 20, wherein each said at least one transducer has a spherical surface.

22. A method according to claim 20, wherein each said transducer is shaped like a polar cap.

23. An ultrasound hyperthermia unit including an ultrasound transducer assembly which directs ultrasonic energy toward a target disposed at a predetermined target location with respect to said assembly, wherein the assembly comprises a plurality of ultrasound transducers which are divergent in the near field because of their shape and arranged radially of a central axis and thereby provide a treatment area which includes said target location about said central axis and adjacent said transducers in the near field; wherein each said transducer has an outwardly convex curvature.

24. A unit according to claim 23, wherein each said transducer has a spherical surface.

25. A unit according to claim 23, wherein each said transducer is shaped like a polar cap.

* * * * *